(12) United States Patent
Kara et al.

(10) Patent No.: US 7,228,167 B2
(45) Date of Patent: Jun. 5, 2007

(54) METHOD AND APPARATUS FOR DETECTING VAGUS NERVE STIMULATION

(75) Inventors: Tomas Kara, Rochester, MN (US); Virend K. Somers, Rochester, MN (US)

(73) Assignee: Mayo Foundation for Medical Education, Rochester, MN (US)

( * ) Notice: Subject to any disclaimer, the term of this patent is extended or adjusted under 35 U.S.C. 154(b) by 83 days.

(21) Appl. No.: 10/821,778

(22) Filed: Apr. 9, 2004

(65) Prior Publication Data

US 2004/0260356 A1 Dec. 23, 2004

Related U.S. Application Data

(60) Provisional application No. 60/462,147, filed on Apr. 10, 2003.

(51) Int. Cl.
*A61B 5/0428* (2006.01)
(52) U.S. Cl. ............... 600/509; 607/2; 607/27
(58) Field of Classification Search ............ 607/1, 607/2, 6, 62; 600/508, 510, 554
See application file for complete search history.

(56) References Cited

U.S. PATENT DOCUMENTS

| | | | |
|---|---|---|---|
| 3,863,625 A | 2/1975 | Viglione et al. | |
| 4,334,545 A | 6/1982 | Shiga | |
| 4,702,254 A | 10/1987 | Zabara | |
| 4,867,164 A | 9/1989 | Zabara | |
| 4,878,498 A | 11/1989 | Abrams et al. | |
| 4,989,610 A * | 2/1991 | Patton et al. | 600/508 |
| 5,222,494 A | 6/1993 | Baker, Jr. | |
| 5,269,302 A | 12/1993 | Swartz et al. | |
| 5,351,394 A | 10/1994 | Weinberg | |
| 5,738,104 A * | 4/1998 | Lo et al. | 600/521 |
| 5,928,272 A * | 7/1999 | Adkins et al. | 607/45 |
| 6,341,236 B1 * | 1/2002 | Osorio et al. | 607/45 |

* cited by examiner

*Primary Examiner*—George R. Evanisko
*Assistant Examiner*—Michael Kahelin
(74) *Attorney, Agent, or Firm*—Terri S. Flynn; Quarles & Brady (57) ABSTRACT

A method and apparatus for monitoring the application of a vagus nerve stimulation signal includes a detection circuit having an amplifier, a filter, and a signal prolongation circuit. The signal prolongation circuit rectifies a detected vagus nerve signal and provides the signal to a Schmitt trigger extending the length of the signal. Because of the prolongation of the signal, the signal can be sampled at a relatively low rate, and real time data illustrating the response of various physiological signals to the application of the vagus nerve signal can be monitored, thereby providing clinical data for monitoring and adjusting the applied stimulation.

13 Claims, 5 Drawing Sheets

METHOD AND APPARATUS FOR DETECTING VAGUS NERVE STIMULATION

CROSS-REFERENCE TO RELATED APPLICATION

This application claims the benefit of provisional application Ser. No. 60/462,147 filed Apr. 10, 2003, entitled "Detection of Vagus Nerve Stimulator Activity", hereby incorporated by reference.

STATEMENT REGARDING FEDERALLY SPONSORED RESEARCH OR DEVELOPMENT

BACKGROUND OF THE INVENTION

The vagus nerve is one of the twelve cranial nerves that originate in the brain. The nerve fibers in the vagus carry information to and from the brain to the larynx, the heart, the stomach, lungs and esophagus, and may also be connected to the limbic structures in the brain, which are associated with the regulation of mood. The vagus nerve, therefore, plays a key role in neural control of body functions, e.g. neural, cardiovascular, respiratory and metabolic functions, and therapies which include stimulation of the vagus nerve have been developed to provide therapy for a number of diseases including epilepsy, anxiety disorders, obesity, pain, cognition and memory disorders as well as cardiovascular, sleep, and breathing disorders.

It has been shown, for example, that the introduction of stimulation control signals to the vagus nerve can modify hyperactivity in the brain, and therefore provide therapeutic benefits for the diseases and conditions described above. The superposition of such corrective measures inhibits the normal progress of a seizure and can prevent seizures altogether. It is also possible that control signals of proper magnitudes when applied to associated neural tracts can cause neural activity to return to a normal state. Corrective signals of this type can be generated by appropriate electrical pulses or waves applied to neurons.

To provide the appropriate stimulus of the vagus nerve, implantable vagus nerve stimulators (VNS), such as those described in U.S. Pat. No. 4,702,254, have been developed. These devices include a pulse generator which is implanted subcutaneously in the patient, and is connected to the vagus nerve with an electrode or electrodes, which are also implanted in the patient. One such system, for example, is the commercially-available VNS therapy system produced by Cyberonics® of Houston, Tex., which consists of a pulse generator, electrode leads, and a programming wand for programming the pulses generated. The pulse generator is surgically implanted in subcutaneous tissue in the upper chest region. The lead is placed in a subcutaneous tunnel that runs from the pulse generator to the vagus nerve, and an electrode connects the lead to the vagus nerve. The generator can be telemetrically interrogated and programmed using a programming wand and associated software as described, for example, in U.S. Pat. No. 5,222,494 to Baker, and U.S. Pat. No. 5,928,272 to Adkins. The programming wand, therefore, can be used to establish a therapeutic stimulation for the patient. It can also be used, in a special mode, to provide a signal indicating the onset of stimulation. The special mode, however, requires operation of a frequency of 5 Hz or below, whereas stimulation frequencies are typically 20-30 Hz. Furthermore, the data is provided in an asynchronous serial link and cannot, therefore, be monitored in conjunction with other physiological signals.

While these commercially-available systems have therefore been successful in providing therapeutic pulses to the vagus nerve to provide therapy for mitigating the effects of a number of diseases, these devices present certain difficulties as they do not provide any means for monitoring the application of a therapeutic stimulating pulse once the device is implanted. Because it is not possible to monitor the pulse as it is applied, it is difficult for care providers to correlate the stimulation of the vagus nerve with the response of the patient, which can be manifested as a physiological change in the patient (i.e. ECG, EEG, blood pressure, breathing, etc.). Because of these problems, it is difficult for care providers to establish an appropriate dose-response relationship for VNS therapy, and to monitor the success of a treatment. Adjustment of the VNS device settings for an individual patient is therefore a major clinical issue.

Moreover, while devices for non-invasive monitoring of biological signals are available, these devices are typically intended for use in monitoring signals such as, for example, electrocardiogram (ECG) and/or electroencephalogram (EEG) signals. The EEG or ECG signals, however, vary significantly from those produced by a VNS stimulator device, and these devices therefore cannot be used to monitor VNS pulses. EEG and ECG signals, for example, are continuous biological signals as opposed to artificial VNS pulses, have a significantly higher amplitude than VNS signals, and are much lower in frequency than VNS signals. Techniques commonly employed for EEG and ECG monitors therefore are not useful in monitoring VNS signals.

SUMMARY OF THE INVENTION

In a first aspect, the invention provides a method for detecting a vagus nerve stimulation signal. Electrodes are applied to a patient in proximity to an implanted vagus nerve stimulator, and a vagus nerve stimulation pulse applied by the stimulator to the patient is detected by the electrodes. The detected signal is amplified, and then filtered in a bandwidth selected to eliminate extraneous noise. The output signal is prolonged to allow sampling of the vagus nerve stimulation signal at a relatively low frequency and therefore for an extended period of time. Prior to prolonging the signal, the signal can be rectified to provide a unipolar signal.

In another aspect of the invention, a non-invasive vagus nerve signal detection apparatus is provided. The apparatus includes an electrode for detecting a differential signal indicative of a pulse applied to the vagus nerve, an amplifier for amplifying the detected vagus nerve signal, and a filter for filtering the detected vagus nerve signal from other signals. A rectifier rectifies the detected signal to provide a unipolar output, and the rectified signal is provided to a comparator for comparing the rectified signal to a threshold level, and for providing an output signal at a predetermined value for a predetermined minimum time frame when the rectified signal exceeds the threshold level. The comparator preferably comprises a Schmitt trigger, which provides a prolonged output signal In another aspect of the invention, a method for long-term monitoring of a vagus nerve stimulation signal is provided. The method comprises the steps of applying electrodes to a patient in proximity to an implanted vagus nerve stimulator device to detect a vagus nerve stimulation signal, amplifying the detected vagus nerve stimulation signal, filtering the detected vagus nerve stimulation signal in a bandwidth selected to eliminate extraneous noise and providing a real time vagus nerve signal, comparing the real time vagus nerve signal to a predetermined threshold signal level and retaining the signal at a predetermined output signal level for a period of time selected to provide a prolonged vagus nerve stimulation signal allowing sampling at a lower rate than the real time vagus nerve signal. The prolonged vagus nerve stimulation signal to trigger sampling of at least one other physiological signal, wherein the effect of the vagus nerve stimulation on the at least one other physiological signal is monitored. The monitored physiological signals can include, for example, an electrocardiogram (ECG), an electroencephalogram (EEG), a blood pressure measurement, and a breathing measurement.

These and other objects, advantages and aspects of the invention will become apparent from the following description. In the description, reference is made to the accompanying drawings which form a part hereof, and in which there is shown a preferred embodiment of the invention. Such embodiment does not necessarily represent the full scope of the invention and reference is made therefore, to the claims herein for interpreting the scope of the invention.

DETAILED DESCRIPTION OF THE PREFERRED EMBODIMENTS

Figure 1:
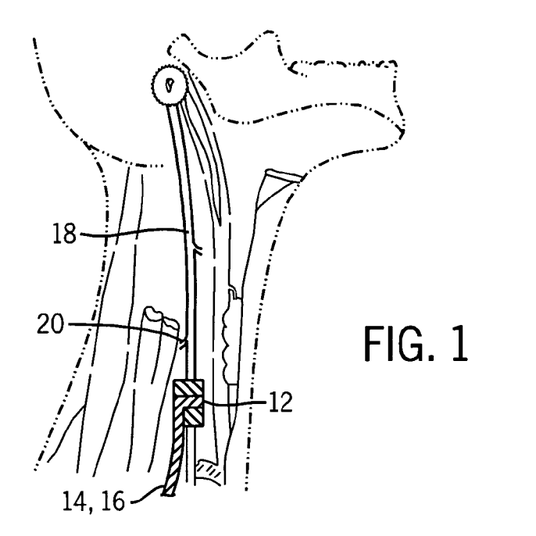
FIG. 1 is a schematic illustration of the placement of an electrode patch on the vagus nerve.
Figure 2:
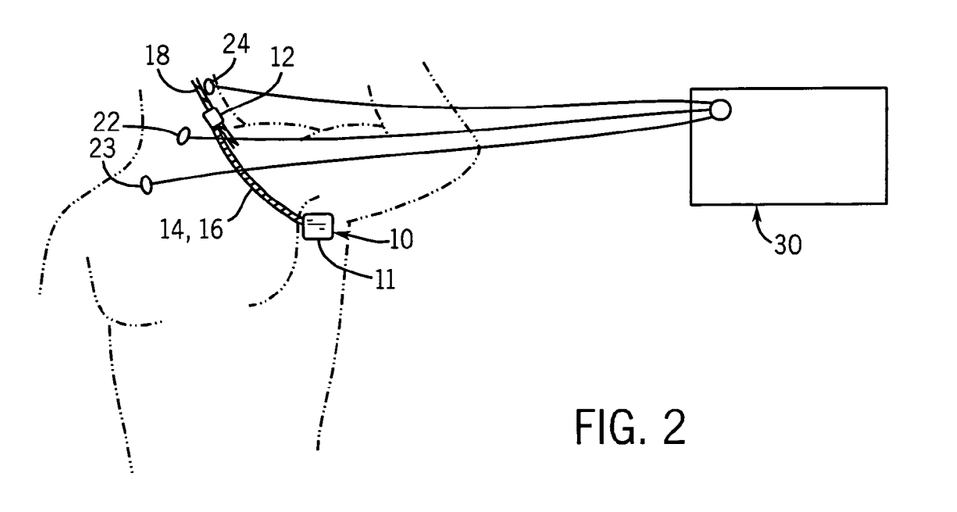
FIG. 2 is a schematic illustration of the placement of the electrode patch of FIG. 1, associated pulse generator in a human body, and detector electrode placement.

Referring now to the figures, and more particularly to FIGS. 1 and 2, a patient with an embedded Vagus Nerve Simulator (VNS) 10 is shown. The VNS 10 includes an electrode patch 12 having both a positive and a negative electrode, and a pair of leads 14 and 16 which lead to a pulse generator 11. The electrode patch 12 is coupled to the vagus nerve 18 at a position below the inferior cardiac nerve 20. Operation of the VNS 10 to stimulate the vagus nerve 18 is described more fully in U.S. Pat. No. 4,702,254, which is hereby incorporated by reference for its description of vagus nerve stimulator devices.

Referring still to FIGS. 1 and 2, to monitor the application of the VNS 10, electrodes 22 and 24 which provide a differential probe are placed on the lateral side of the neck of the patient and on the upper thorax, respectively and are aligned such that they are positioned directly adjacent the electrode patch 12 which connects the vagus nerve 18 to the pulse generator 11. An additional electrode 23 provides a whole body potential reference and is placed on the upper chest region of the patient. Each of the electrodes 22, 23, and 24 are preferably attached directly to the skin surface, such that the signal applied by the pulse generator 11 to the vagus nerve 18 can be detected by the electrodes, which are fed to a VNS signal detector circuit 30, as described below.

Figure 3:
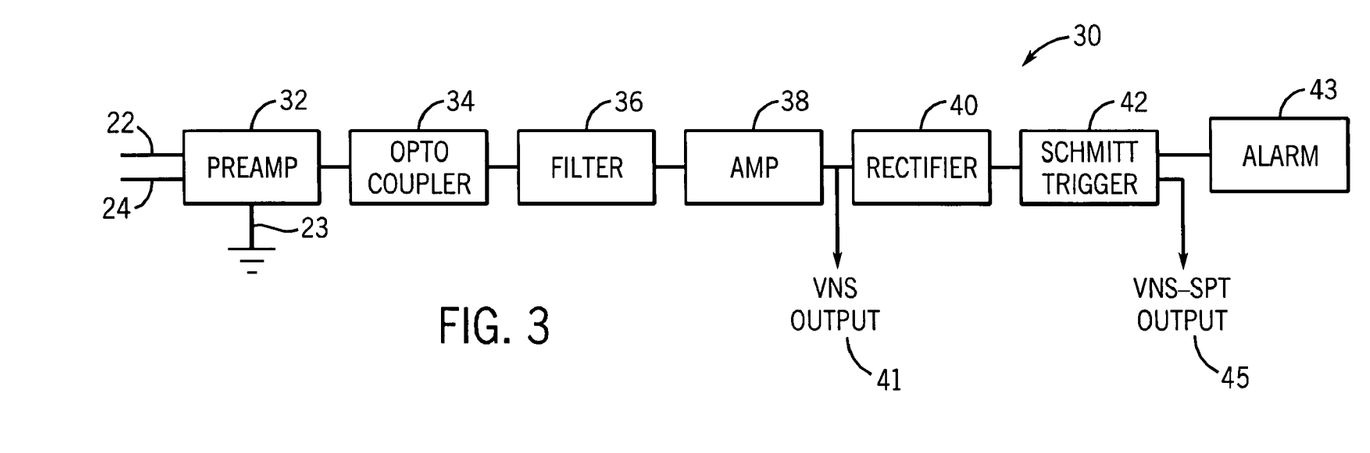
FIG. 3 is a block diagram of a vagus nerve signal detection circuit constructed in accordance with the present invention.

Referring now to FIG. 3, a differential signal sensed between the electrodes 22 and 24 is fed into the VNS signal detector circuit 30 which filters the input signals to determine when a pulse is applied by the pulse generator 11 to stimulate the vagus nerve. At the input stage, the VNS signal detector circuit 30 includes a pre-amplifier 32, which receives the differential input signal between the electrodes 22 and 24 and amplifies the input signal with a fixed gain of two hundred in order to increase the level of the detected signal for processing. The gain of two hundred has been determined experimentally to provide a sufficient gain for many applications, however it will be apparent to one of ordinary skill in the art that the size of the gain is adjustable depending on the components used and also on the dynamic features of the subsequent components in the VNS signal detector circuit 30. The gain to the pre-amplifier 32 can be provided as an adjustable level to allow for adjustment by the user.

The output from the pre-amplifier 32 is next fed to an isolation circuit 34 which can be, for example, an optocoupler, an isolation transformer, or a capacitive coupling device intended to electrically isolate the input signal, which is coupled directly to the patient, from the electrical processing circuits and analysis circuits. The isolation circuit 34 protects the patient from inadvertent contact with electrical components which might result in shock. To provide adequate protection, the isolation circuit is designed to provide isolation for up to 8 kV.

Referring still to FIG. 3, the isolated output signal is next directed to a filter circuit 36, which filters the isolated output signal to eliminate extraneous noise and to extract the VNS signal. Typically, VNS signals are provided as a series of rectangular peaks, each peak having a duration of about 0.13-1.5 milliseconds, and are provided in a frequency band at least 10 kHz. These signals are filtered from environmental noise and other physiological bioelectric signals such as ECG or EEG signals, through the filter circuit 36 which provides a passband filter. The passband filter can be, for example, provided as a combination of fourth-order Butterworth low-pass and high-pass filters, providing a passband of 1 Hz to 20 kHz, although these parameters can be varied depending on the application and, as described above, with reference to the pre-amplifier 32, can be adjustable. When the signal/noise ratio is low, for example, the high pass cut off frequency can be decreased. When employing advanced signal processing techniques, however, the filter has been shown to require a passband of only 5 kHz to 10 kHz to detect the onset edges of stimulation peaks in both polarities. Although a Butterworth filter is described, various methods of providing a passband filter will be apparent to those of skill in the art.

Referring still to FIG. 3, the output signal of the filter 36 is next provided to an amplifier 38, which preferably has a gain range extending between 0 and 80 dB. The amplifier 38 further increases the magnitude of the detected and filtered VNS signal, therefore providing a signal which can be more easily detected and read by processing circuitry. The output of the amplifier 38 therefore provides a filtered and amplified representation of the real time VNS signal, referred to hereafter as the real time VNS signal 41. The real time VNS signal 41 provides a direct representation of the vagus nerve stimulation which can be directly monitored. However, due to the frequency at which these signals are produced, monitoring must be provided at relatively high frequencies of up to 20 kHZ, and the amount of data collected can easily overload the memory of an attached analysis device or computer.

Referring still to FIG. 3, to allow long-term monitoring and synchronous display of the VNS signal with other physiologic signals, as well as to improve the ability to trigger other data acquisitions form the VNS signal, a signal prolongation technique (SPT) is used to provide another, more easily monitored signal, referred to hereafter as the VNS-SPT 45. To provide the VNS-SPT signal, the amplified VNS signal is next provided to a rectifier 40, which provides a unipolar output. The mode of the rectifier 40 can be selected either to provide a half wave positive polarity rectification, full wave rectification, or a half wave negative polarity rectification. The output of the rectifier circuit 40 is provided to a Schmitt trigger circuit 42, which compares the output of the rectifier 40 to a predetermined amplitude reference level 44 which indicates that a VNS signal 41 of sufficient magnitude has been detected. If the rectified input signal exceeds the reference level, the output of the Schmitt Trigger 42 is driven high, and the VNS-SPT signal 45 is normalized to a TTL-level signal of 5 Volts. The high level signal therefore indicates an active vagus stimulation status, while the low level output represents an inactive stimulation status.

Figure 4:
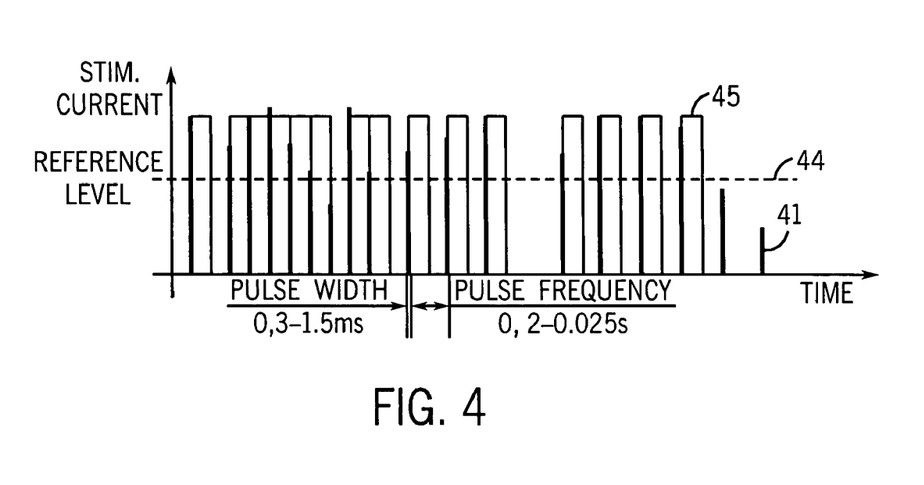
FIG. 4 is a graph illustrating a real time vagus nerve signal and a prolonged vagus nerve signal (VSN-SPT) produced by the circuit of FIG. 3 versus time.

Referring now to FIG. 4, the VNS output and VNS-SPT output are shown on a graph versus time. The VNS pulses 41 are narrow, having a duration of 0.3-1.5 ms, and have an amplitude which varies, but is usually in the range of about 0.05 mV. The frequency bandwidth of the VNS signals 41 is typically between 1 Hz and 20 kHz. To adequately sample the VNS signal 41, as described above, a sampling rate of 20 kHz or above is required.

Also as described above, to produce the more constant VNS-SPT signal 45, the amplitude of the VNS signal 41 is compared to the reference level 44 and, when the amplitude of the VNS signal 41 exceeds the reference level 44, the Schmitt trigger 42 provides a TTL level output signal and maintains the signal at a high level for a period of at least five milliseconds. By maintaining the output at a high level over a period of time, data can be sampled at a significantly lower rate than would be required to sample the data, typically at about 100 Hz and extending up to about 500 Hz. The Schmitt trigger 42 further prolongs the VNS-SPT signal 45 when in the inactive mode for a period of about five milliseconds, thereby providing a stable signal for monitoring of the VNS activity at a low sampling frequency. Although a period of five milliseconds is described, it will be apparent that this period can be varied.

In addition to providing a stable VNS-SPT 45 output signal, the Schmitt Trigger 42 can also trigger an alarm circuit 43 for providing at least one of an audio or a visual indicator, such as, for example, a beeper, a light emitting diode, or a bar graph to provide both acoustic and visual feedback to the user. The audio and visual feedback provide basic monitoring of the onset, duration and termination of the VNS signal 41, thereby allowing an independent check of the stimulation state of the vagus nerve without the need for additional external instrumentation. Audio and visual feedback is particularly useful, for example, in routine clinical practices and settings.

Figure 5:
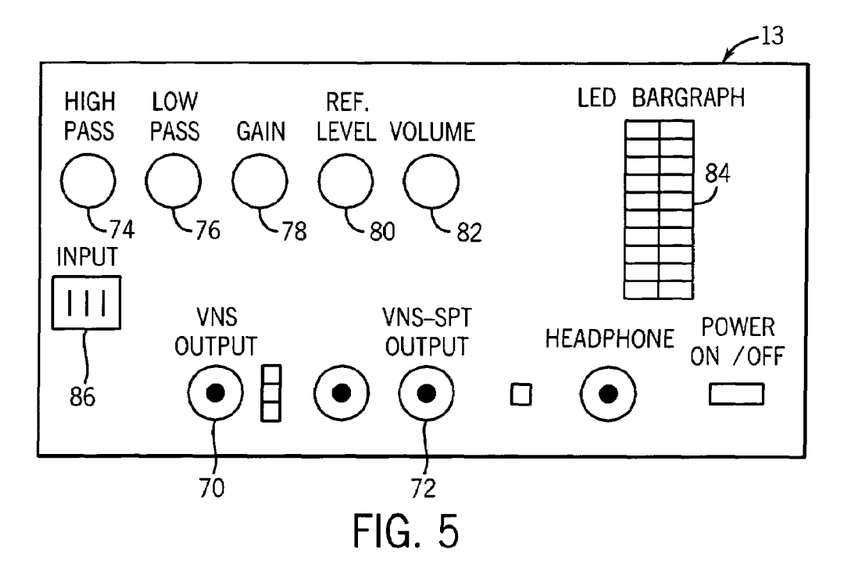
FIG. 5 is a front view of a housing for the circuit of FIG. 4 and illustrating various components.

Referring now to FIG. 5, the analysis circuit 30 can be provided in a housing 13 including an input receptacle 86 for receiving the leads from each of the electrodes 22, 23, and 24, and providing both a VNS output connector 70 for the VNS signal 41 and a VNS-SPT output connector 72 for the VNS-SPT signal 45. The housing can also include a light emitting diode or light emitting diode bargraph 84 for providing a visual signal to the user, which is controlled by the alarm circuit 43 described above, as well as a volume control 82 for controlling an audio "beep", also as described above. The housing 13 can also include controls for a user to vary the high pass cut off 74 and low pass cutoff 76 of the filter circuit 36, the gain 78 of the preamplifier 32 and/or amplifier 38, and the reference level 80 for triggering the Schmitt Trigger 42, thereby allowing for changes in the detection circuit 30 based on environmental or other considerations. The VNS and VNS-SPT output connectors 70 and 72 can be coupled directly to an oscilloscope or medical monitoring device to provide triggering or segmenting of acquired data for analysis, as described below.

Figure 6:
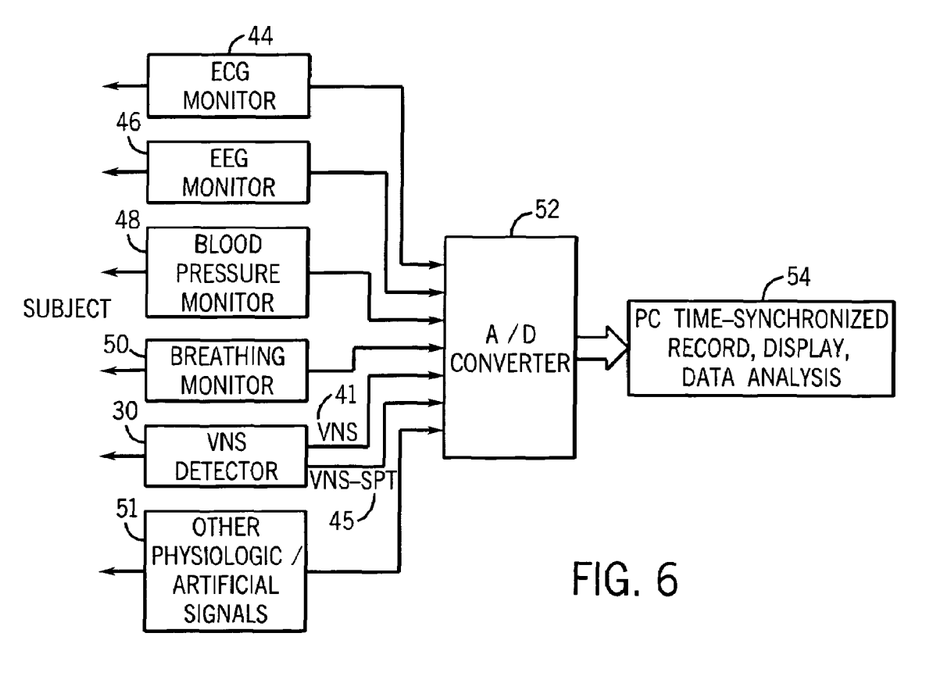
FIG. 6 is a block diagram of an analysis circuit including a controller for receiving the SPT signal as well as various physiological signals and providing signal processing and analysis of the signals.

Referring now to FIG. 6, the output VNS signal 41 and the VNS-SPT signal 45 from the VNS signal detector circuit 30 can be provided to external monitoring circuitry to provide both monitoring and analysis of the application of a stimulation of the vagus nerve and an associated response. As shown, the VNS signal 41 and/or VNS-SPT signals 45 are monitored in conjunction with a number of other physiological parameters, including an ECG monitor 44, an EEG monitor 46, a blood pressure monitor, 48, a breathing monitor 50, and other devices providing physiological or artificial signals. As shown in FIG. 5, the output signals of each of the ECG monitor 44, EEG monitor 46, blood pressure monitor 48, breathing monitor 50, and other physiological monitoring devices are analog signals, which are fed to an analog to digital converter 52, along with the output of the detector circuit 30 which can provide both the VNS signal 41 and the VNS-SPT signal 45. Although the VNS-SPT signal is shown as provided to the A/D converter 52, it will be apparent that, as this signal is a TTL level digital signal at the output of the analysis circuit 30, the VNS-SPT 45 signal can also be provided directly to an analysis system. Although any commercially-available A/D converter can be employed for purposes of providing a digital output signal from the analog input signals, to obtain proper resolution, a 12 bit or higher A/D converter is preferred. The A/D converter 52 can also be provided as part of data acquisition tool including signal processing and conditioning elements such as the 16 input A/D converter, data acquisition (DAQ) PC card commercially available from National Instruments, Inc, of Austin, Tex., USA.

Figure 7:
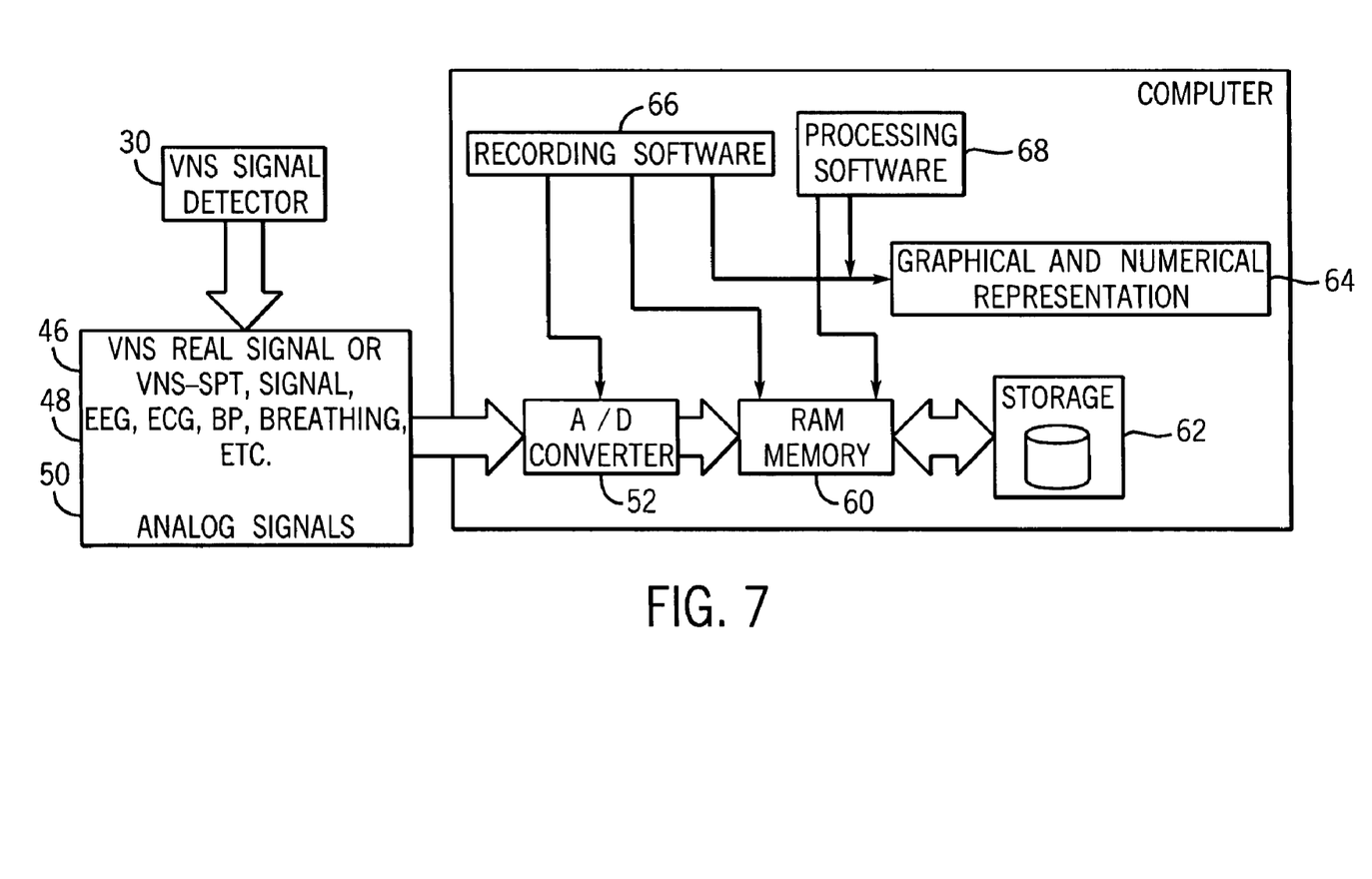
FIG. 7 is an alternative embodiment of an analysis circuit of FIG. 6.

Referring still to FIG. 6, the digitalized signals from the A/D converter are provided to a computer 54 or other programmable analysis device having the capability of processing, analyzing, and displaying data. Referring now also to FIG. 7, a second embodiment of a computer 54 in which the A/D converter 52 is provided as part of a computer system 54 is shown. Here, the computer 54 includes the A/D converter 52, a memory component 60 for temporary data storage, a hard drive or other long-term data storage 62, and a display 64 capable of providing both graphical and numerical data output. The controller 54 can include software both for recording 66 and processing 68 the acquired data from each of the analog input signals 44, 46, 48, and 50 and the VNS signal 41 and VNS-SPT signal 45.

Figure 8:
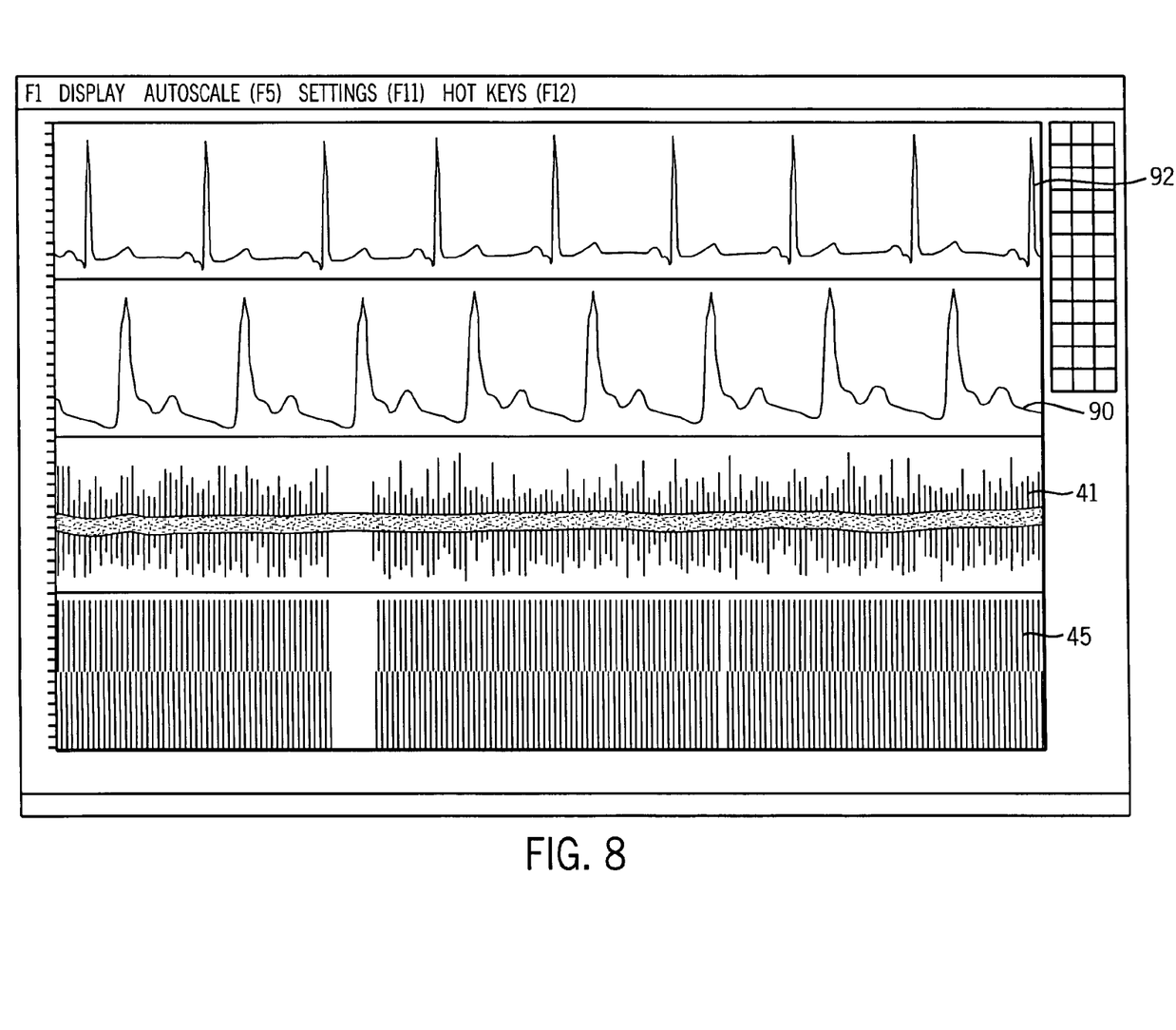
FIG. 8 is an illustration of a display coupled to the analysis circuits of FIG. 6 or 7 and providing a display of the physiological signals versus the vagus nerve signal and VNS-SPT signals produced by the analysis circuit of FIG. 3.

Referring now to FIG. 8, a typical monitoring process is shown on the display 64. Here, a blood pressure signal 90 scaled in mmHg is shown along with an EEG signal 92 in mV, the VNS signal 41, and the VNS-SPT signal 45. As described above, the VNS signal 41 can be sampled at a sampling frequency of up to 100 kHz or more, depending on the available storage capacity. While providing an accurate analysis of applied pulse data, the VNS signal 41 is therefore not suitable for long term monitoring, as the amount of data required to be stored can quickly overload the memory components of most analysis devices. For long term monitoring, the modified VNS-SPT signal 45 is preferably sampled, as this signal can be sampled at a significantly lower sampling frequency, and therefore data can be sampled, stored, and analyzed over a significantly longer period of time without overloading memory. The VNS-SPT signal 45 has, for example, been sampled experimentally in a range extending between 100 and 500 Hz.

In the computer 54, the VNS and biological signals can be processed, analyzed, and displayed on a monitor 64 to allow for evaluation of the effects of the VNS 10 on the physiological health of the patient. Data acquisition can be segmented or triggered based on the VNS 41 or VNS-SPT 45 signals, and then processed either as data is acquired or off-line. The processed data can be saved in short term memory 60 or in long term memory 62, or displayed on display 64. Typical processing software for the acquired data can include, for example, rectangular signal filtration of all or selected channels employing both direct and indirect complex Fast Fourier Transformation, analysis of the amplitude, frequency, and time domain characteristics of the acquired data averaging to provide the arithmetic mean of all selected segments in all channels, to improve the signal to noise ratio by square root of the number of segments analyzed. As described above, data processing and analysis software can be provided on a personal computer, or as part of a medical analysis device such as the ANNAlab® ScopeWin produced by St. Anne's University Hospital Brno, Czech Republic. The ANNAlab® ScopeWin system includes an analog to digital converter as well as processing software for processing and analyzing acquired data as shown in FIG. 7.

The present invention therefore provides the ability for medical practitioners to monitor the application of VNS stimulation and the resultant response non-invasively, and therefore provides the opportunity for a neurosurgeon to test the function and setting of the VNS 10 during and immediately after the surgery. Algorithms for optimally setting the VNS could also be used. Similarly, the function of the VNS 10 can be tested during regular visits at a clinic or doctor's office. The system also permits very precise synchronization of VNS activity with other physiological signals. Therefore, data segmentation and averaging techniques can be used to increase the signal to noise ratio, and it is possible to assess very small changes and reactions caused by stimulation of the vagus nerve. The resolution of the circuit 30 further enables differentiation of phase coherent events evoked by the VNS device 10 in EEG and other signals.

Importantly, the present invention allows the monitoring of VNS stimulation over a period of time. This capability has a number of important clinical applications in the treatment of epilepsy, cardiovascular disease, and sleep disorders. By monitoring the application and the resultant reaction, optimization of the stimulation intensity applied by the VNS device 10 during treatment of epilepsy can be achieved. Presently, there are no objective criteria for optimal settings of stimulation parameters in the treatment of epilepsy. Recent studies have shown, for example, that approximately 35% of patients treated with VNS therapy exhibited a decline in seizure frequency for 50%. or more. However, prior to the development of the present invention, it was not possible to determine why some patients respond to VNS therapy favorably while others do not. Using the present invention, it was possible to determine that patients who respond well to VNS therapy and who have a significant decrease of epileptic seizure also exhibit a direct correlation between the effect of stimulation and EEG activity. Patients who do not respond to VNS therapy do not exhibit a change in EEG during the stimulation. Using the present invention, it is possible to optimize the parameters of vagus nerve stimulation for individual patient up to levels which lead to significant changes in EEG signals, and can more easily achieve an optimal level of stimulation soon after implantation of the VNS 10.

Analysis of the direct effect of vagus nerve stimulation on the cardiovascular system using the present invention has also yielded important results. The vagus nerve plays a crucial role in heart rate and blood pressure regulation. The effect of vagus nerve stimulation on heart rate and blood pressure can be analyzed directly with the present invention. This analysis has shown that a decrease in the heart rate and/or blood pressure are the two most worrisome adverse effects of VNS therapy. Therefore, an assessment of the effects of vagus nerve stimulation on the heart rate and blood pressure of an individual patient can also be used to optimize stimulation parameters for treatment of epilepsy. It is conceivable that this approach will allow to maximize therapeutic effects while minimizing potential adverse effects on the cardiovascular system or other systems. This type of measurement is particularly important in groups of patients such as children, who have developing central nervous systems and cardiovascular systems and are therefore known to exhibit unpredictable side effects during VNS therapy. Furthermore, for patients who do not respond well to the standard intensity level of stimulation, the present invention can be used to completely readjust or increase the treatment. If the VNS were approved also for treatment of obesity and/or depression and/or cardiovascular diseases, analysis of effects of stimulation on the cardiovascular system in these patients will be essential, because all of these groups are at high risk for negative cardiovascular side effects.

Analysis of the direct effect of vagus nerve stimulation on the respiratory system can also potentially be applied in the treatment of sleep related breathing disorders (SRBD), as the vagus nerve also plays an essential role also in the regulation of both the frequency and the depth of breathing. Using the present invention, therefore, it is possible to analyze the direct effects of stimulation on breathing frequency and depth during both daytime and night. This analysis may be useful in represent a new way in the treatment of obstructive and particularly central sleep apnea. This theory is based on our original data from sleep studies in patients with implanted VNS where we observed in some of subjects significant increase of breathing frequency during stimulation.

The present invention can also be used in other types of research applications. Patients with an implanted VNS, for example, can be used in studies of the role of the autonomic nervous system in general and the vagus nerve (parasympathetic nervous system) in particular. Potential research applications include studies of the effects of vagus nerve stimulation on heart rate and blood pressure during daytime and sleep; the effects of vagus nerve stimulation on myocardial electrophysiology (esp. PQ and QT intervals); the effect of vagus nerve stimulation on sleep (daytime and sleep studies). The effect of vagus nerve stimulation on brain functions and brain electrophysiology (daytime and sleep studies). The effect of vagus nerve stimulation on respiratory system, possibly a role in the treatment of obstructive and central sleep apnea. The positive and negative interactions of vagus nerve stimulation with cardiovascular and neurological drugs. The effect of vagus nerve stimulation in treatment of cardiovascular, metabolic, neurologic and psychiatric disorders.

While a specific analysis circuit 30 has been shown and described, various methods of detecting and processing the VNS signal will be apparent to those of skill in the art. For example, while the electrodes described above detect a voltage level of the applied VNS pulse, a current detecting device capable of detecting current flow caused by the VNS device 10 could also be used. Furthermore, while specific filtering and triggering devices have been described, it will be apparent that various methods and devices for providing these functions are available.

Hence, it should be appreciated that various modifications of the above described embodiment may be made without departing from the spirit or scope of the following claims. Thus, the claims should be looked to in order to assess the full scope of the invention.

The invention claimed is:

1. A method for non-invasive detection of a vagus nerve stimulation signal, the method comprising the following steps:
    applying external electrodes to a patient in proximity to an implanted vagus nerve stimulator;
    detecting a vagus nerve stimulation signal applied by the stimulator to the patient with said electrodes;
    amplifying the detected vagus nerve stimulation signal;
    filtering the detected vagus nerve stimulation signal in a bandwidth selected to eliminate extraneous noise; and
    prolonging the detected signal to allow sampling of the vagus nerve stimulation signal and to trigger sampling of at least one other physiological signal to allow for monitoring the effect of the vagus nerve stimulation on the at least one other physiological signal.

2. The method as defined in claim 1, further comprising the step of comparing the detected vagus nerve stimulation signal to a threshold level prior to prolonging the vagus nerve stimulation signal.

3. The method as defined in claim 1, further comprising the step of electrically isolating the amplified input signal.

4. The method as defined in claim 1, further comprising the step of rectifying the filtered signal.

5. The method as defined in claim 1, further comprising the step of producing an alarm signal providing at least one of a visual or an audio signal to a user indicating that the vagus nerve stimulation signal has been detected.

6. The method as recited in claim 1, further comprising the step of retaining the filtered signal at a predetermined output signal level for a period of time selected to provide a prolonged vagus nerve stimulation signal allowing sampling of a lower rate than the filtered signal.

7. The method as defined in claim 1, further comprising the step of electrically isolating the detected vagus nerve stimulation signal from the filtered vagus nerve stimulation signal and the prolonged vagus nerve stimulation signal.

8. The method as defined in claim 2, further comprising the step of rectifying the filtered vagus nerve stimulation signal prior to the step of comparing the filtered vagus nerve stimulation signal to the threshold value.

9. The method of claim 1, further comprising the step of detecting an analog signal representative of at least one electrocardiogram (EGG), an electroencephalogram (EEG), a blood pressure measurement, and a breathing measurement.

10. The method as defined in claim 9, further comprising the step of electrically connecting each of the vagus nerve stimulation signal and the physiological signal to a controller, the controller being programmed to monitor the physiological signal as a function of the vagus nerve signal.

11. The method as defined in claim 10, further comprising the step of storing at least one of the filtered and the prolonged vagus nerve stimulation signal and the physiological signal as a function of time.

12. The method as defined in claim 10, further comprising the step of displaying the physiological signal and the at least one of the filtered and the prolonged vagus nerve stimulation signal.

13. The method as defined in claim 12, further comprising the step of providing at least one of a visual and an audio output when the prolonged vagus nerve stimulation signal is detected.

* * * * *

UNITED STATES PATENT AND TRADEMARK OFFICE
CERTIFICATE OF CORRECTION

PATENT NO. : 7,228,167 B2 Page 1 of 1
APPLICATION NO. : 10/821778
DATED : June 5, 2007
INVENTOR(S) : Tomas Kara et al.

It is certified that error appears in the above-identified patent and that said Letters Patent is hereby corrected as shown below:

Claim 9, Line 22, Column 10
"electrocardiogram (EGG)" should be
--electrocardiogram (ECG)--

Signed and Sealed this

Twenty-third Day of October, 2007

JON W. DUDAS
*Director of the United States Patent and Trademark Office*